US006976637B2

United States Patent
Massimo

(10) Patent No.: US 6,976,637 B2
(45) Date of Patent: Dec. 20, 2005

(54) PERFUMING DEVICE PROVIDED WITH DROP-COLLECTOR, FOR VEHICLES

(75) Inventor: De Pietri Massimo, Cardi (IT)

(73) Assignee: De Leuriks B.V., Amsterdam (NL)

( * ) Notice: Subject to any disclaimer, the term of this patent is extended or adjusted under 35 U.S.C. 154(b) by 169 days.

(21) Appl. No.: 10/387,085

(22) Filed: Mar. 12, 2003

(65) Prior Publication Data

US 2003/0180194 A1 Sep. 25, 2003

(30) Foreign Application Priority Data

Mar. 22, 2002 (IT) ..................................... MO2002A0069

(51) Int. Cl.⁷ ............................................... A24F 25/00
(52) U.S. Cl. ............................. 239/44; 239/57; 239/34; 239/326; 239/145
(58) Field of Search ............................. 239/34–60, 326, 239/145; 422/123, 124; 454/156, 157, 158; D23/366, 370

(56) References Cited

U.S. PATENT DOCUMENTS

| | | | | |
|---|---|---|---|---|
| 2,556,608 A | * | 6/1951 | Will | 239/47 |
| 4,200,229 A | * | 4/1980 | Spector | 239/57 |
| 4,523,870 A | * | 6/1985 | Spector | 454/157 |
| 4,840,773 A | * | 6/1989 | Wade | 422/124 |
| 6,416,043 B1 | * | 7/2002 | Eisenbraun | 261/104 |

* cited by examiner

*Primary Examiner*—Dinh Q. Nguyen
(74) *Attorney, Agent, or Firm*—Notaro & Michalos PC

(57) ABSTRACT

It is the matter of a perfuming device for vehicles to be put, through a suitable fork, on the tabs of the air grille.

To always maintain the perpendicularity, the fork can take, by rotating on itself, eight different positions. The bottle of the perfumed essence is housed into a shell which is hermetically closed in its lower part and apt to contain any possible dripping from the wick. Bottle and shell, together, form the disposable recharge, without the hands come into direct contact with any essence leakage.

2 Claims, 1 Drawing Sheet

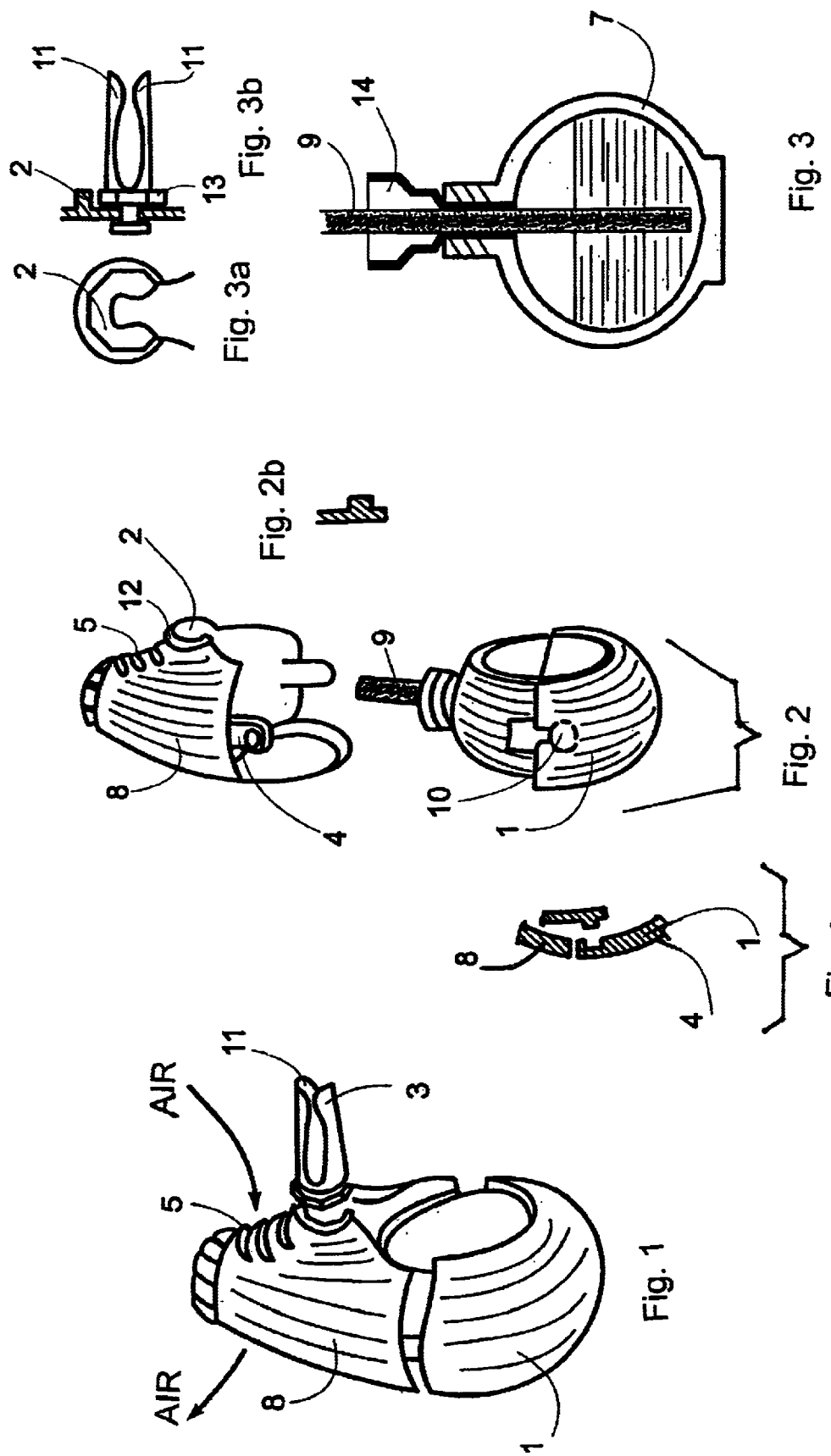

PERFUMING DEVICE PROVIDED WITH DROP-COLLECTOR, FOR VEHICLES

The perfuming devices, usually used in vehicles, show the drawback not to collect the drops, if any, falling from the wick. They are provided with forks for connection to the air tabs, with a fixed positioning, preventing thereby their correct use on the non-orthogonal and/or vertical tabs of the grilles.

This invention wants to eliminate these drawbacks by rendering easier the use and application thereof.

The invention will be better understood from the following detailed description, given with reference tot he enclosed drawings in which:

FIG. 1 shows, the perfuming device of the invention, in assembled position;

FIG. 2, is an exploded view of the device of FIG. 1 with FIGS. 2a and 2b being details in section;

FIG. 3 shows the bottle of a perfuming device of the invention, with the wick and the drop collector fitted, with FIGS. 3a and 3b being details of FIG. 3.

With reference to FIG. 1, the perfuming device of the invention consists of the following parts:

a shell 1, winding round a bottle 7 as better visible in FIG. 2, which is to be connected with an upper portion 8.

The lower portion 1 and the upper portion 8 are assembled to form a housing for the bottle 7 of the perfume.

The upper portion 8 is formed by a shell on which there are the openings 5 on the back to allow the air passage through and around a wick 9 see FIGS. 1 and 2).

The shell 1 is connected to the shell 8 by means of tongues provided on the lower shell, as per reference 10 of FIG. 2 and as sshown in detail in FIGS. 2a and 2b.

A fork 3, which, as already told, supports the whole through the tabs of the air vent, consists of two jaws 11 (FIG. 3b) and has to be mounted on the shell 8, where a forepart 12 is provided, having a recess with the form of an octagon with a hole in the center (FIG. 3a) and a vertical slot, the whole being referenced 2. Into the hole the rear portion of the fork has to be inserted, provided with an octagonal nut 13 which is housed in the female octagon of the forepart 12.

The positioning of the fork can take place by removing it from the forepart and repositioning the same in the desired position or should an elastic material be used for the forepart, the fork can rotate likewise with a light effort, causing it to take the desired position.

FIG. 3 shows the bottle with the wick 9 and the drop collector 14 fitted therein.

The wick is inserted into the drop-collector having the form of a funnel.

Should the funnel-shaped container be insufficient and the essence overflow, the lower shell 8 of the housing, would collect the liquid surplus.

The details of construction can be widely change from the description and the drawings without departing from the scope of this invention.

What is claimed is:

1. Perfuming device with drop-collector for vehicles, comprising a housing for a perfuming bottle (7) to be applied to a vent grid of a vehicle, wherein said housing consists of two shells (1, 8), one of which, a lower one (1), contains said perfuming bottle and further comprising support means (3) which can be positioned in several different positions with respect to the housing, said support means consisting of a fork (3), said fork being rotatable around its own axis and being provided with a polygonal base (13) inserted into a polygonal hole (12) of the housing, to allow positioning of said fork by rotating said fork around said axis and wherein the two shells, the lower one (1) and an upper one (8), are kept together by means of tongues (4).

2. Perfuming device with drop-collector for vehicles, comprising a housing for a perfuming bottle (7) to be applied to a vent grid of a vehicle, wherein said housing consists of two shells (1, 8), one of which, a lower one (1), contains said perfuming bottle and further comprising support means (3) which can be positioned in several different positions with respect to the housing, said support means consisting of a fork (3), said fork being rotatable around its own axis and being provided with a polygonal base (13) inserted into a polygonal hole (12) of the housing, to allow positioning of said fork by rotating said fork around said axis and wherein the lower shell (8) housing the bottle (7) which forms a disposable recharge, functions as a drop-collector.

* * * * *